(12) United States Patent
Weiss et al.

(10) Patent No.: US 12,721,304 B2
(45) Date of Patent: Sep. 1, 2026

(54) WIRELESS DIGITAL TREATMENT AND WARNING SYSTEM AND DISPLAY FOR VETERINARIAN ANIMAL CAGES

(71) Applicant: Mitchell Weiss, Los Angeles, CA (US)

(72) Inventors: Mitchell Weiss, Los Angeles, CA (US); Thomas Wang, Alhambra, CA (US); William F. Ryczek, La Verne, CA (US)

( * ) Notice: Subject to any disclaimer, the term of this patent is extended or adjusted under 35 U.S.C. 154(b) by 0 days.

(21) Appl. No.: 18/762,419

(22) Filed: Jul. 2, 2024

(65) Prior Publication Data

US 2024/0349692 A1 Oct. 24, 2024

Related U.S. Application Data

(63) Continuation-in-part of application No. 17/544,317, filed on Dec. 7, 2021, now Pat. No. 12,027,263.

(60) Provisional application No. 63/122,786, filed on Dec. 8, 2020.

(51) Int. Cl.
*A01K 1/03* (2006.01)
*G16H 10/65* (2018.01)
*G16H 40/00* (2018.01)

(52) U.S. Cl.
CPC ............ *A01K 1/031* (2013.01); *G16H 10/65* (2018.01); *G16H 40/00* (2018.01)

(58) Field of Classification Search
CPC ......... G16H 10/65; G16H 40/00; A01K 1/031
See application file for complete search history.

(56) References Cited

U.S. PATENT DOCUMENTS 6,397,190 B1 * 5/2002 Goetz .................. G06F 15/025 235/375
9,210,755 B2 12/2015 Grajcar
11,330,793 B1 * 5/2022 Sloan ..................... A01K 1/031
11,367,519 B1 * 6/2022 Heldman ............. A61M 5/142
2004/0217858 A1 11/2004 Ingley, III et al.
2006/0253299 A1 * 11/2006 Konishi ................ G06Q 10/10 705/2

(Continued)

FOREIGN PATENT DOCUMENTS

CN 206878872 1/2018
CN 207948505 10/2018

(Continued)

*Primary Examiner* — Kimberly S Berona
*Assistant Examiner* — Katherine June Walter
(74) *Attorney, Agent, or Firm* — Eric Karich; Karich & Associates

(57) ABSTRACT

A system for assisting a veterinarian in caring for an animal has a veterinarian animal cage having a cage body and a door that allows access to the cage body. The system further has a computer with a wireless data communication device, and a display screen, the computer being mounted on the veterinarian animal cage. The system further has a central server being operably connected with the computer and having a management program and a database for storing the information about the animals, and for transmitting information related to the animal housed in the veterinarian animal cage to the computer, so that the information may be visually outputted on the display screen. The computer receives input from the veterinarian, and transmits the input to the central server where it is stored in the database of the central server.

7 Claims, 8 Drawing Sheets

(56) References Cited

U.S. PATENT DOCUMENTS

| | | | | |
|---|---|---|---|---|
| 2012/0085291 | A1 | 4/2012 | Conger et al. | |
| 2016/0246934 | A1 * | 8/2016 | Dunlop | G16H 70/20 |
| 2017/0088035 | A1 * | 3/2017 | Williams | B60Q 1/0094 |
| 2017/0097169 | A1 | 4/2017 | Azevedo et al. | |
| 2018/0137247 | A1 * | 5/2018 | Bore | G16H 80/00 |
| 2018/0330813 | A1 * | 11/2018 | Garber | G16H 40/20 |
| 2020/0037583 | A1 * | 2/2020 | Grajcar | A01K 31/22 |
| 2022/0180075 | A1 * | 6/2022 | Temkin | H04L 67/12 |

FOREIGN PATENT DOCUMENTS

| | | | |
|---|---|---|---|
| EP | 2 364 079 | | 9/2011 |
| EP | 2 627 169 | | 8/2013 |
| EP | 2 950 637 | | 12/2015 |
| EP | 3 005 869 | | 4/2016 |
| EP | 3 013 141 | | 5/2016 |
| EP | 3 129 906 | | 2/2017 |
| EP | 4 449 861 | | 10/2024 |
| WO | 2007149528 | | 12/2007 |
| WO | 2018039366 | | 3/2018 |
| WO | 2018094098 | A2 | 5/2018 |
| WO | 2022125689 | A1 | 6/2022 |
| WO | 2022251609 | | 12/2022 |

* cited by examiner

WIRELESS DIGITAL TREATMENT AND WARNING SYSTEM AND DISPLAY FOR VETERINARIAN ANIMAL CAGES

CROSS-REFERENCE TO RELATED APPLICATIONS

This application for a utility patent is a Continuation-in-part of U.S. application Ser. No. 17/544,317, filed Dec. 7, 2021, which claims the benefit of U.S. Provisional Application No. 63/122,786, filed Dec. 8, 2020.

BACKGROUND OF THE INVENTION

Field of the Invention

This invention relates generally to veterinarian systems for treatment and care of animals, and more particularly, to a wireless digital treatment and warning system and display for veterinarian animal cages.

Description of Related Art

Presently, veterinarian offices typically use informal means of communication with staff regarding the course of treatment for animals under the care of a veterinarian doctor. Typical veterinarian animal treatment/care protocols are often provided in hand-written notes that are delivered to the staff members, or simply left on or near a cage of an animal. Course of treatment is typically stored in desktop computers that are separate from the cage, not on the cage itself, so somebody must take the written notes to the desktop computer and enter them manually, which is labor intensive, and also a source of errors.

Furthermore, paper-based notes and instructions can be damaged, obscured, lost, or otherwise rendered difficult or impossible to follow. Furthermore, a staff member may not know of a note left from a prior staff member, and may not notice it in time.

There are no existing devices or systems that provide all of the benefits of the present invention. The current system enables veterinarians to access all information about an animal, its vitals etc., notes about treatment and medications, and information about the course of treatment, at the cage. The system also provides a picture of the animal to prevent confusion, the name of the animal, the owners name, the breed, sex, weight. The software app of the present invention houses everything related to the animal, also including treatment, records. And it enables the owner of the animal to check the animal in by filling out an intake form and reserve a cage space. The owner therefore does much of the clerical work to check in the animal through the app so it can be displayed on the device at the cage and also, everything displayed at the cage is also stored in the veterinary management system of a central computer.

There is a long-felt need in the field for a centralized system that enables superior care for the animal, including a better way to receive a course of treatment, at the actual cage, and to provide instruction for the care and treatment of animals housed in the veterinarian animal cages.

SUMMARY OF THE INVENTION

The present invention teaches certain benefits in construction and use which give rise to the objectives described below.

The present invention provides a system for assisting a veterinarian in caring for an animal. The system comprises a veterinarian animal cage having a cage body and a door that allows access to the cage body. The system further has a computer with a computer processor, a computer memory, a wireless data communication device, and a display screen, the computer being mounted on the veterinarian animal cage. The system further has a central server with a computer processor and a computer memory, the central server being operably connected with the computer, the central server having a management program and a database installed in the computer memory for storing the information about the animals, and for transmitting information related to the animal housed in the veterinarian animal cage to the computer, so that the information may be visually outputted on the display screen. The computer receives input from the veterinarian, and transmits the input to the central server where it is stored in the database of the central server.

A primary objective of the present invention is to provide a wireless digital treatment and warning system having advantages not taught by the prior art.

Another objective is to provide a system that enables a veterinarian or other caregiver to enter a course of treatment for an animal in a specific cage, while the veterinarian or other caregiver is physically with the animal at the cage. This information is available to be viewed by others, such as registered veterinary technicians, and any other staff or other persons that might require the information.

A further objective is to provide a system that includes a microphone for enabling voice to text transcription in real time, and also provides tools for properly formatting the information, and artificial intelligence for reviewing the data for errors.

A further objective is to provide a system that proactively provides warnings to caregivers to ensure that care is correctly provided in a safe manner for both the animal and caregiver.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention.

DETAILED DESCRIPTION OF THE INVENTION

The above-described drawing figures illustrate the invention, an animal treatment system for veterinarian animal cages. The animal treatment system includes a digital display panel along which one or more display screens are disposed, for displaying information pertaining to an animal being housed in the cage.

Figure 1:
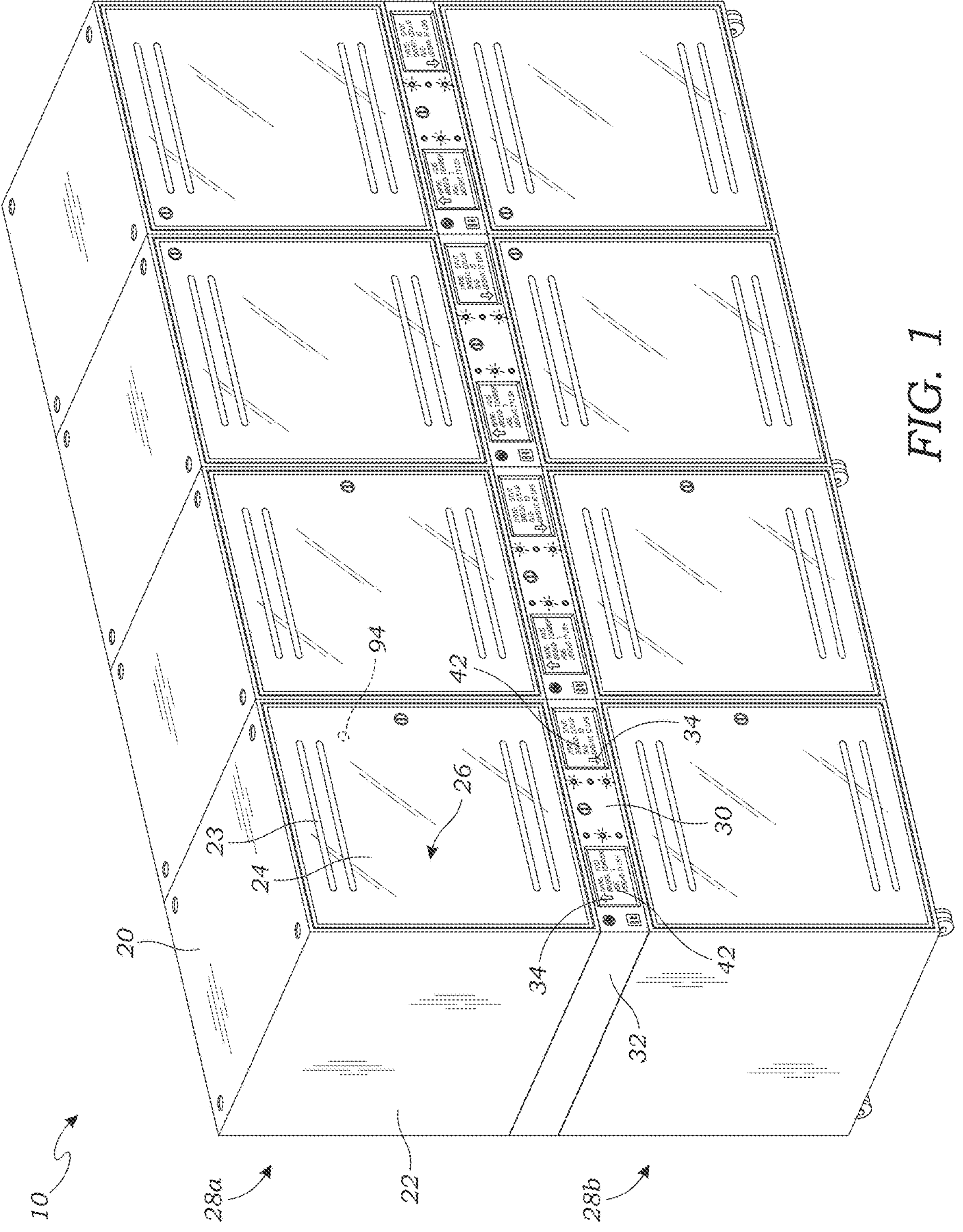
FIG. 1 is a perspective view of an animal treatment system according to one embodiment of the present invention.
Figure 2:
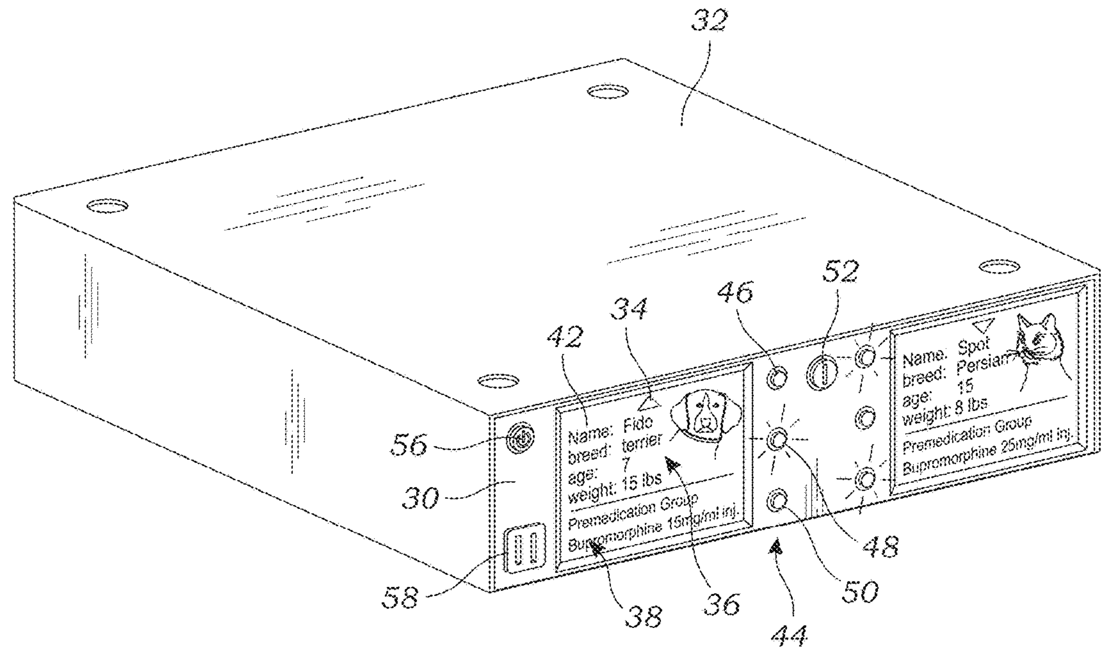
FIG. 2 is a perspective view of a digital display panel of the system mounted on a cuboid housing.

FIG. 1 is a perspective view of an animal treatment system 10 according to one embodiment of the present invention, and FIG. 2 is a perspective view of a digital display panel 30 of the system 10 mounted on a cuboid housing 32. As shown in FIGS. 1-2, the system 10 comprises at least one veterinarian animal cage 20, and a computer 40 having a display screen 42 for displaying information about an animal within the cage 20, each component being discussed at length below. The computer 40 is adapted to display information and receive input from a veterinarian, to assist the veterinarian with caring for the animal without needing to leave the cage area and gather or copy information on a separate computer device/notation means, discussed further below.

As illustrated, the animal cage 20 may be provided alone or in an arrangement of multiple cages, which may be stacked, positioned side-by-side, or provided in any other suitable arrangement. In this embodiment, there are four top cages 28A mounted atop four bottom cages 28B, with the digital display panel 30 mounted therebetween. However, the animal cage 20 may be provided as a standalone cage. The computers 40 are mounted to the digital display panel 30, which is positioned so that each of the display screens 42 is associated with one of the cages. In this case, with one cage on top, one cage on the bottom, and the panel in between, one of the panels is associated with the top cage 28A and the other is associated with the bottom cage 28B. A visual indicator, such as an arrow 34, may be displayed on the screens, to indicate the cage associated with the screen. Alternatively, the arrow 34 could also be printed adjacent the screen, or other forms of indicators may be used, including displays on the screen, the physical location of the screen, etc. Furthermore, other arrangements of screens and cages may be used, so long as a user can determine the association. A single cage and a single screen may be used together, and/or any other arrangement, some of which are discussed in greater detail below.

As shown in FIGS. 1-2, each cage 20 comprises a cage body 22 and a cage door 24 that allows access to an internal chamber 26 of the cage body 22. In this embodiment, the cage door 24 may be a front, hinged door, but in other embodiments, the cage door 24 may be positioned on the side, top, or bottom of the cage 20, or there may be multiple doors. Furthermore, the cage door 24 may slide or detach instead of having a hinged connection to the cage body 22. In some embodiments, the cage door 24 may include ventilation holes or slots 23, or similar features known in the art. Various different animal cages may include darkened walls, or transparent, translucent, or opaque walls, depending on the needs of the animal. For example, if an animal is excited by other animals, an opaque cage may be used to reduce visibility. Alternatively, if an animal is made anxious by an enclosed space or being alone, they may be placed in a cage with some visibility. Since the general construction of such cages is well known in the art, they are not described in greater detail herein.

In this embodiment, the digital display panel 30 is pivotally mounted on the cuboid housing 32, the cuboid housing 32 being physically mounted on the veterinarian animal cage 20, wherein the computer 40 is mounted to the digital display panel 30 of the cuboid housing 32. In some uses, the computer 40 may function to control operation of cage 20 electronically, e.g., may lock/unlock the cage door 24, control temperature (heating, cooling, fan), interior lighting, etc. In some embodiments, the system 10 (sometimes through third-party devices) can measure the temperature in the cage 20, and in some cases manually actuate a fan or heater (heat is sometimes required after surgery to help stabilize the animal). The cage 20 may also transmit a live or recorded video or still picture to the owner, etc.

In some embodiments, the digital display panel 30 is a steel material. In some embodiments, a size of the digital display panel 30 is approximately seven vertical inches by thirty horizontal inches. In some other embodiments, the size of the steel digital display panel 30 is approximately seven horizontal inches by thirty vertical inches.

As illustrated, the display screen 42 displays animal identification information 36, specifically the following: the animal's name and age, and a picture of the animal; the owner's name (and in some cases contact information, notes, etc.); vital signs, including weight, pulse rate, and temperature (collected by other devices). Other identification information may also be displayed, or specific data points may be excluded. In some embodiments, a scale (not shown) may be included in the internal chamber 26 of the cage body 22, so the weight displayed on the display screen 42 is measured in real-time. In some embodiments, the system 10 functions in conjunction with a sensor vest (not shown) that the animal wears, wherein the sensor vest is adapted to transmit collected data (i.e., vitals) to the computer 40.

The display screen 42 may also display treatment information 38: medication information, dietary information and feeding times, etc., e.g., 5 grams of food for animal in cage every four hours, one dose of medication X at noon for the animal, etc. The display screen 42 may also display alerts for various situations (e.g., aggressive behavior, NPO status before surgery).

In some embodiments, one or more colored warning LEDS 44 are mounted on the digital display panel 30, apart from the computer 40, which are operably connected to the computer 40 to provide a visual warning alert that it is presently time to medicate, time to feed, not medicate/feed, when an animal is aggressive, or indicate a problem in vital signs of the animal.

In this embodiment, the colored warning lights 44 include a medicate light 46 to indicate when medication should be administered, and an aggressive warning light 48 to indicate if the animal is aggressive, and special care must be taken. The colored warning lights 44 may further include a check vitals light 50 that alerts the caregiver to check the animal's vitals, and/or take any other actions that may be required. These lights 44 may be separate lights (e.g., LEDs) as illustrated, or they may be displayed on the display screen 42. The number of lights, how they are displayed, and other factors may be varied by one skilled in the art without departing from the present invention and should be considered within the scope of the claims. In one embodiment, in which the warning notices are displayed on the display screen, this screen may be designated a "home screen," which is displayed as a default screen, so that important information tends to remain readily visible, unless the screen is being actively used for other purposes.

While the-above described components may be separately available to obtain by a person, these existing components (such as the steel digital display panel 30, the display screen/s 42, and the warning lights 44) are combined together in a novel way. The animal treatment system 10 uses the novel combination of the components in connection with the veterinarian animal cage 20 to provide a better way for treatment, medication administration, and monitoring of vital signs of an animal with fewer mistakes resulting in improved medical care and treatment of the animal.

Figure 3:
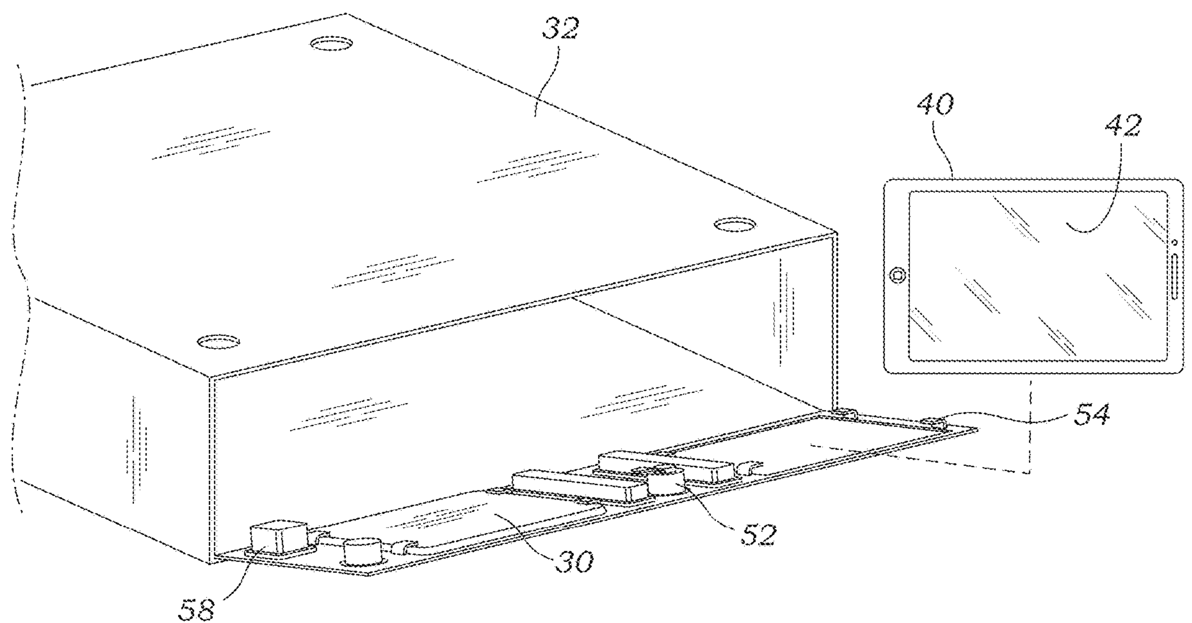
FIG. 3 is a perspective view similar to FIG. 2, but showing the digital display panel in an open position.

FIG. 3 is a perspective view similar to FIG. 2, but showing the digital display panel 30 in an open position. As shown in FIG. 3, the digital display panel 30 may be pivotally mounted on the cuboid housing 32, the cuboid housing 32 being physically mounted on the veterinarian animal cage 20, wherein the computer 40 is mounted to the digital display panel 30 of the cuboid housing 32. In this embodiment, the pivotally mounted display panel 30 may include a latch 52 and/or lock for retaining the display panel 30 in the closed position (FIGS. 1-2.). In another embodiment, the display panel 30 may be mounted in other ways to enable access to the housing 32.

As illustrated in FIG. 3, the cuboid housing 32 may be opened (via hinges, slide-opening, detachment, or similar), exposing a retainer mechanism 54 of the display panel 30. In this embodiment, the retainer mechanism 54 is in the form of a plurality of angled tabs, but in other embodiments may be in the form of rails, hook-and-loop fasteners, brackets, straps, etc. The computer 40 is slidably mounted on the retainer mechanism 54, wherein the computer 40 is in the form of a tablet computer. However, a smart phone or similar device may also be slidably mounted in the retainer mechanism 54 of FIG. 3. In other embodiments, the rest of the computer 40 may be provided separately from the display screen 42, or be connected to a power source (not shown), and may wirelessly communicate with any outside computers, lights, and/or other accessories.

As illustrated, in this embodiment, the cuboid housing 32 may further include a power switch 56 for turning the system 10 on and off, as well as a power outlet 58 which enables caregivers to plug in other electronic devices and tools for use in or adjacent the cages 20, and/or for powering the system 10.

Figure 4:
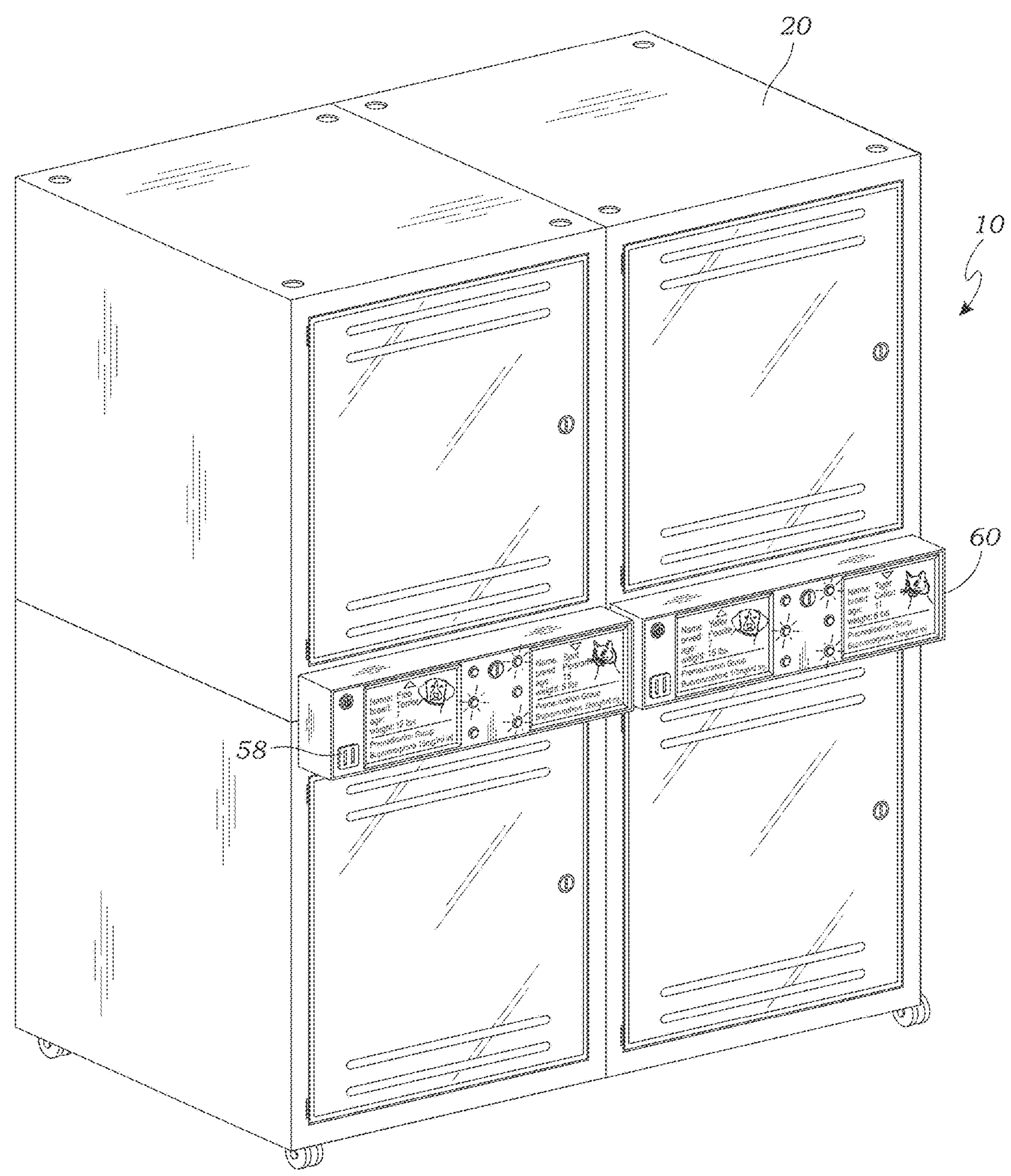
FIG. 4 is a perspective view of a second embodiment of the cuboid housing, shown mounted to animal cages.
Figure 5:
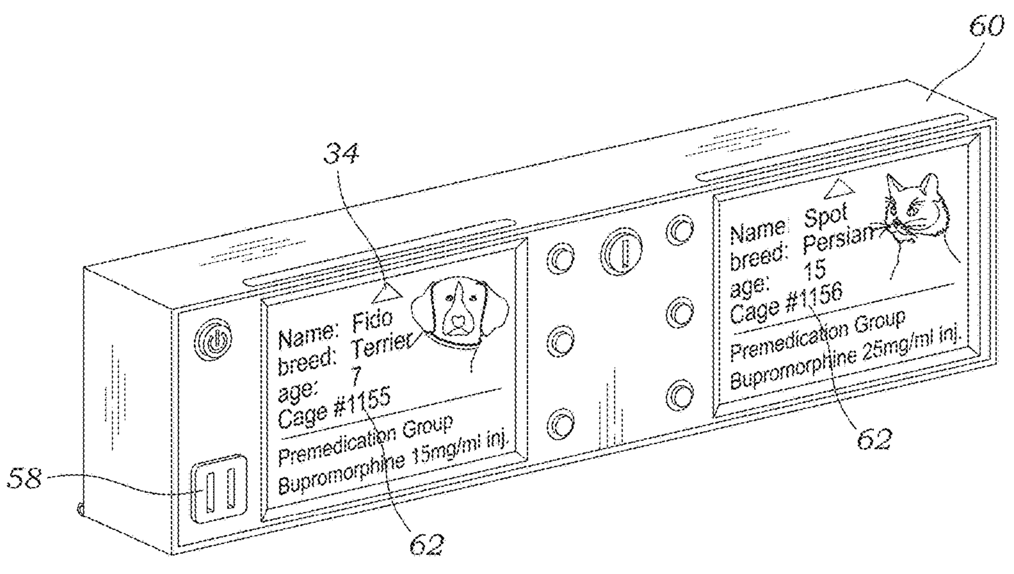
FIG. 5 is a perspective view thereof, without the animal cages.

FIG. 4 is a perspective view of a second embodiment of the cuboid housing 60 of the computer 40 shown mounted to the animal cages 20, and FIG. 5 is a perspective view of the cuboid housing, without the animal cages 20. As shown in FIGS. 4-5, in this embodiment, the cuboid housing 60 is smaller and adapted to be mounted on the front of the cages 20, such as between the top and bottom cages in a horizontal configuration, as shown, or alternatively, between them in a vertical configuration (not shown).

As shown in FIG. 5, the display screen 42 may display a cage number 62 for identifying the associated cage 20. In some embodiments, the system 10 associates the cage number 62 with stored data for the course of treatment and prescription medication information for a particular animal in the animal cage 20, along with other suitable information (e.g., owner name and contact information, associated veterinarian, medical history, etc.). As illustrated, the arrow 34 may also be displayed for identifying the associated cage 20.

Figure 6:
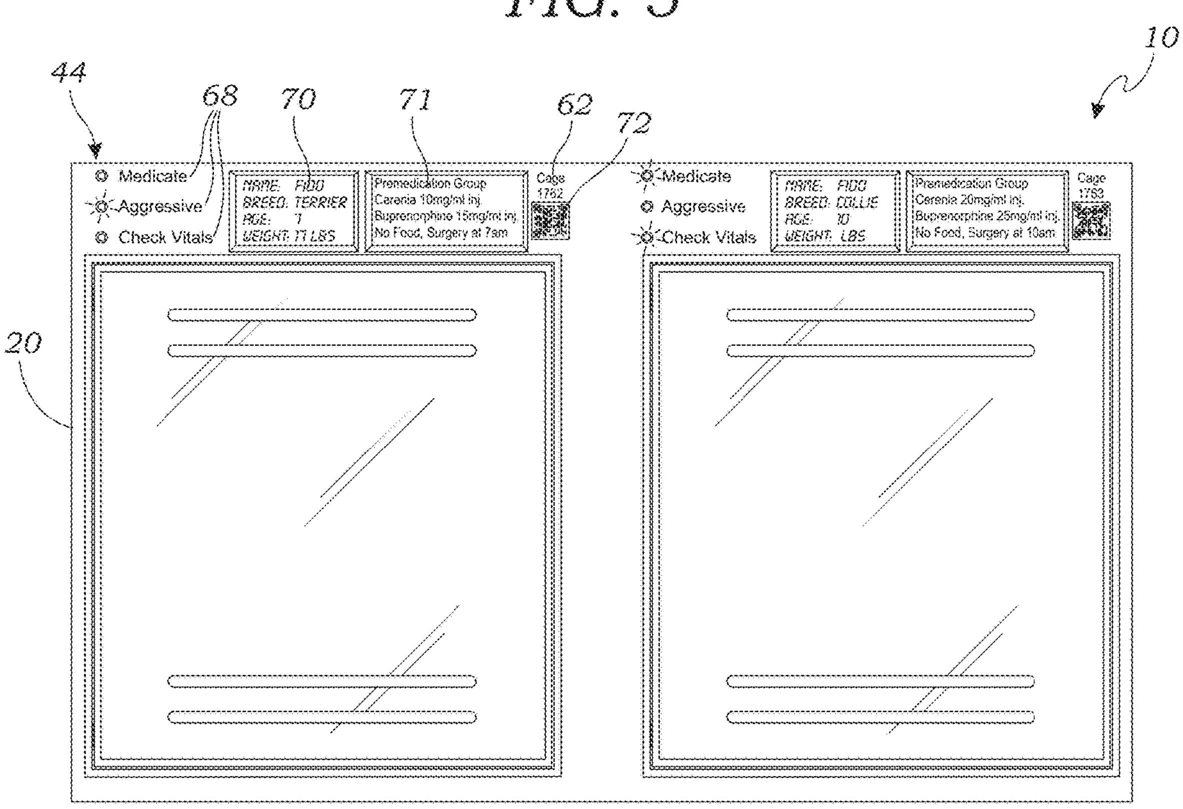
FIG. 6 is a front elevation view of a second embodiment of a digital display panel.

FIG. 6 is a front elevation view of a second embodiment of the digital display panel 60. In this embodiment, the digital display panel 60 is built into the top of the cage 20. This embodiment shows the plurality of warning lights 44 such as are described above, but with labels 68 beside each light 44. This embodiment further includes two screens for displaying information, a first screen 70 and a second screen 71 (although any number of displays may be used, in any arrangement desired). In this embodiment, the cage code is printed on the cage 20 itself, and there is also a code 72 (e.g., QR code) printed on the cage 20, so that the cage number 62 may be determined automatically by capturing the image of the QR code 72, and automatically directed to a suitable downloadable app or web page.

Figure 7:
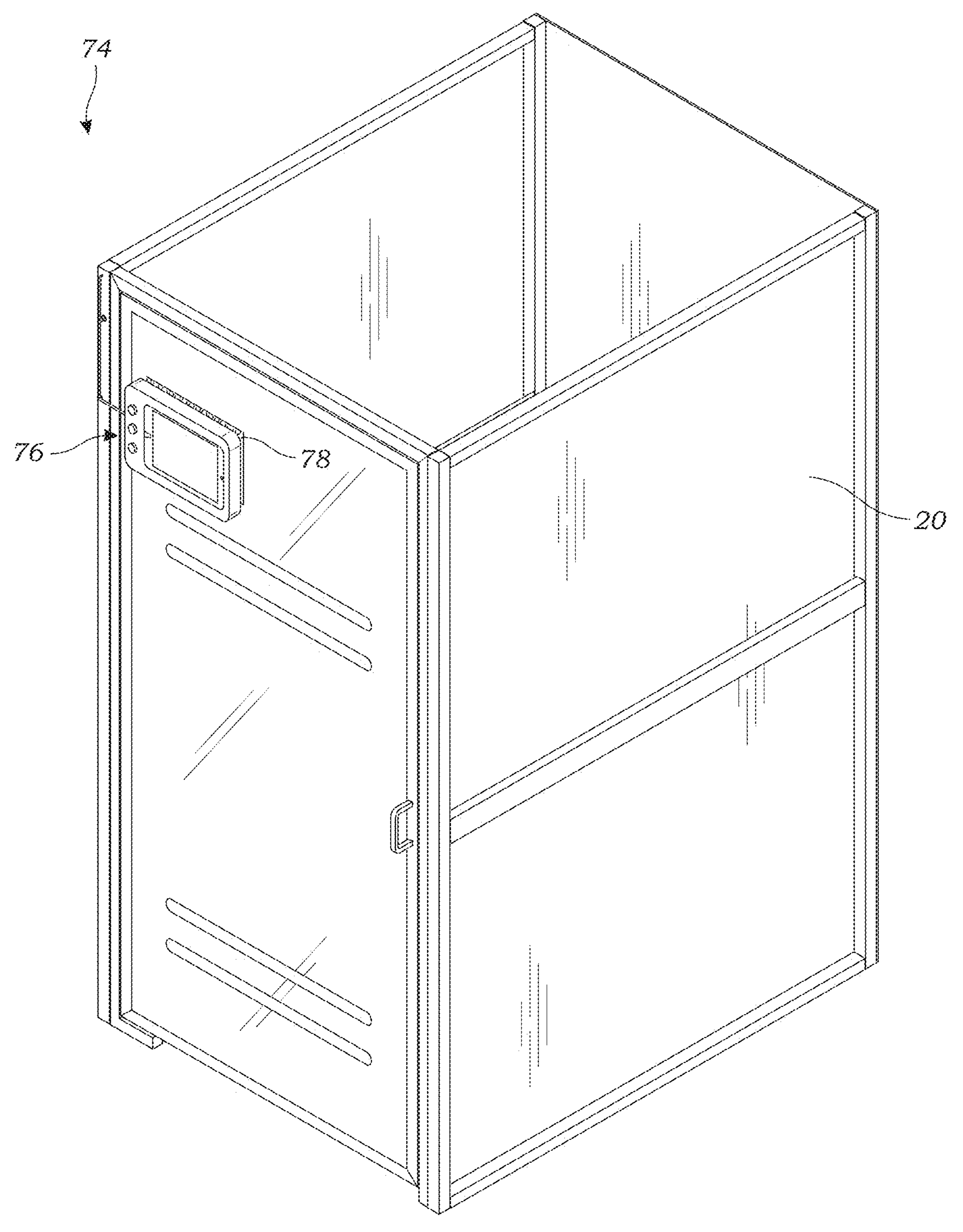
FIG. 7 is a perspective view of a second embodiment of the animal treatment system.

FIG. 7 is a perspective view of a second embodiment of the animal treatment system 74. In this embodiment, the system 74 has a smaller display unit 76 which may be mountable (removably or permanently) onto the cage 20 with a fastener 78 (e.g., hooks and loops fasteners, suction cups, adhesives, mechanical fasteners, and/or any other fasteners known in the art).

Figure 8:
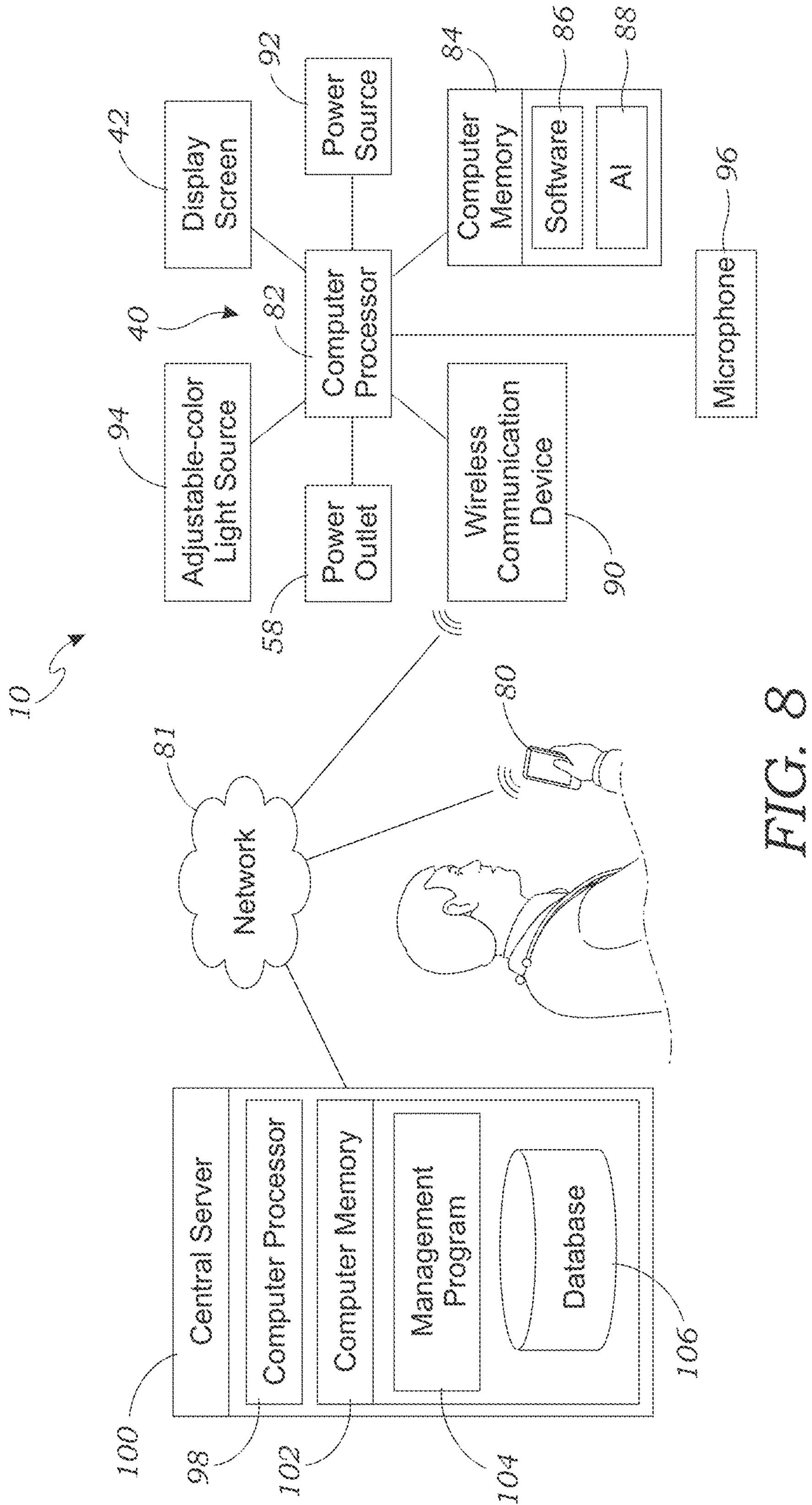
FIG. 8 is a block diagram of the system of FIG. 1, and a veterinarian using a smart phone to update the system.

FIG. 8 is a block diagram of the animal treatment system 10 of FIG. 1, illustrating a veterinarian using a smart phone 80 to update the system 10. As shown in FIG. 8, the system 10 comprises the computer 40 that communicates with a central server 100 via a network 81 (e.g., global computer network, LAN, and/or any other form of communication network known in the art). The computer 40 of the system 10 includes a computer processor 82 and a computer memory 84 which has operably installed thereupon software 86 for operating the system 10, the software 86 being discussed further below. The computer memory 84 may also include an AI program 88, also discussed further below. The system 10 may further include a wireless data communication device 90 for communicating with the network 81. While a smart phone 80 is illustrated, it should be understood that the claimed system 10 can function without any additional devices.

As illustrated, the computer 40 includes the display mechanism. In some embodiments, the computer 40 may be operably attached to a power source 92 (typically an AC outlet in the office, as known in the art). The system 10 may include the power outlet 58 discussed above. In this embodiment, the computer 40 is also operably connected (e.g., wired, wireless, etc.) to an adjustable-color light source 94 such as an LED device, or an LED strip, which is positioned within the animal cage 20 (as shown in FIG. 1). The adjustable-color light source 94 functions to indicate a warning about the aggressiveness of the animal, to indicate that the animal requires medication, and or any other indication known in the art. For example, the adjustable-color light source 94 might illuminate the cage 20 with red to warn that the animal is aggressive or upset, orange to indicate that the animal needs to be administered a drug or receive some form of treatment, blue to indicate he or she does not get food, etc. Obviously, any color scheme may be used, according to the product designer's determinations and instructions.

As illustrated in FIG. 8, the computer 40 may further include a microphone 96. The microphone 96 may be used with voice-to-text functionality in the software 86 for use by the veterinarian, discussed further below. Alternatively, the veterinarian could use a microphone of the smart phone 80 (not shown), wherein the text readout would be wirelessly transferred to the computer 40.

In one embodiment, the app may be operated exclusively by voice controls received via the microphone, so that no keyboard or other input mechanism is required. This is discussed in greater detail below.

In this embodiment, the central server 100 comprises a computer processor 98 and a computer memory 102, the central server 100 being operably connected with the computer, the central server 100 having a management program and a database 106 installed in the computer memory 102 for storing the information about the animals, and for transmitting information related to the animal housed in the veterinarian animal cage 20 to the computer 40, so that the information may be visually outputted on the display screen 42. The computer 40 receives input from the veterinarian, and transmits the input to the central server 100 where it is stored in the database 106 of the central server 100.

The management program for central administration of the system 10 enables cage codes to be added, amended, updated, removed, etc. It also enables users (e.g., caregivers, veterinarians, etc.) to input data, enter treatment regimes, etc. It may also be accessible by pet owners for entering data, accessing medical records/care instructions/discharge information, monitoring their pet and/or his or her treatment, paying invoices, scheduling appointments, submitting questions, etc. In some embodiments, the owner may be able to watch the examination remotely, and ask questions/provide information throughout. The database 106 may be provided for storing all of this data and making it available to the system 10. In some embodiments, the management program 104 may enable the conducting of medical exams at the site of the animals (home). The owner may remotely perform clerical work, e.g., reserving a cage 20 and inputting the animal information and medical record.

The system 10 may operate autonomously and rely on its own custom programming, and it may also be linked to existing practice management software systems (e.g., CORNERSTONE®, EXYVET®, etc.). When veterinarians or other caregivers enter information into the system 10, not only is the information available at the cage 20, this information may also be automatically entered into the existing practice management software system, thereby saving time and effort to re-enter the data into a desktop system. This dual system also functions as a backup of the data, so the failure of one system will not result in the loss of the data.

The system 10 also functions to facilitate transfer of information between veterinarians or other caregivers when they are making rounds, coming, going, or a new person is brought in, etc. The transfer typically occurs at the cage 20, where the veterinarian or other caregiver discusses the case with the new person. The system 10 enables an easy transfer, as the data is all there on the screen, and no notes need to be transferred.

For purposes of this application, the terms "computer," "computer device," "server," and similar terms, refer to a device and/or system of devices that include at least one computer processor, and some form of computer memory having a capability to store data. The computer may comprise hardware, software, and firmware for receiving, storing, and/or processing data as described below. For example, a computer may comprise any of a wide range of digital electronic devices, including, but not limited to, a server, a desktop computer, a laptop, a smart phone 80, a tablet, or any form of electronic device capable of functioning as described herein.

The term "computer processor" as used herein refers to an electrical component that performs operations on an external data source, such as a computer memory, typically in the form of a microprocessor, although any equivalent structure may be used.

The term "computer memory" as used herein refers to any tangible, non-transitory storage that participates in providing instructions to a processor for execution. Such a medium may take many forms, including hut not limited to, non-volatile media, volatile media, and any equivalent media known in the art. Non-volatile media includes, for example, ROM, magnetic media, and optical storage media. Volatile media includes, for example, DRAM, which typically serves as main memory. Common forms of computer memory include, for example, hard drives and other forms of magnetic media, optical media such as CD-ROM disks, as well as various forms of RAM, ROM, PROM, EPROM, FLASH-EPROM, solid state media such as memory cards, and any other form of memory chip or cartridge, or any other medium from which a computer can read. While several examples are provided above, these examples are not meant to be limiting, but illustrative of several common examples, and any similar or equivalent devices or systems may be used that are known to those skilled in the art.

The term "database" as used herein, refers to any form of one or more (or combination of) relational databases, object-oriented databases, hierarchical databases, network databases, non-relational (e.g. NoSQL) databases, document store databases, in-memory databases, programs, tables, files, lists, or any form of programming structure or structures that function to store data as described herein.

The wireless communication device may be any form of communications hardware or software known in the art for enabling communications via a network. The network 81 may include any device or system for communicating information from one computer device to another. For example, a global computer network (e.g., the Internet) may be used, including any form of local area networks (LANs), wide area networks (WANs), direct connections, such as through a universal serial bus (USB) port, other forms of computer-readable media, or any combination thereof. On an interconnected set of LANs, including those based on differing architectures and protocols, a router may act as a link between LANs, enabling messages to be sent from one to another. In addition, communication links within LANs typically include twisted wire pair or coaxial cable, while communication links between networks may utilize analog telephone lines, full or fractional dedicated digital lines, Digital Subscriber Lines (DSLs), wireless links including satellite links, or other communications links known to those skilled in the art. The network 81 may further include any form of wireless network, including cellular systems, WLAN, Wireless Router (WR) mesh, or the like. Access technologies such as 3G, 4G, 5G, and future access networks may enable wide area coverage for mobile devices. In essence, the wireless network 81 may include any wireless communication mechanism known in the art by which information may travel between computers of the present system.

The network 81 may include any device or system for communicating information from one computer device to another. For example, a global computer network (e.g., the Internet) may be used, including any form of local area networks (LANs), wide area networks (WANs), direct connections, such as through a universal serial bus (USB) port, other forms of computer-readable media, or any combination thereof. On an interconnected set of LANs, including those based on differing architectures and protocols, a router may act as a link between LANs, enabling messages to be sent from one to another. In addition, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. The network 81 may further include any form of wireless network, including cellular systems, WLAN, Wireless Router (WR) mesh, or the like. Access technologies such as 2G, 3G, 4G, and future access networks may enable wide area coverage for mobile devices. In essence, the wireless network 81 may include any wireless communication mechanism known in the art by which information may travel between computers of the present system.

The system server may include one or more servers, desktop computers, multiprocessor systems, microprocessor-based or programmable electronics devices, network appliances, or any form of equivalent device(s) known in the art. The system computer may be in the form of a single device, or multiple devices. The system server may be distributed over a plurality of network devices and/or implemented using cloud architecture. The system server may operate using a master/slave approach over a plurality of network devices, within a cluster, a peer-to-peer architecture, and/or any of a variety of other architectures.

Figure 9:
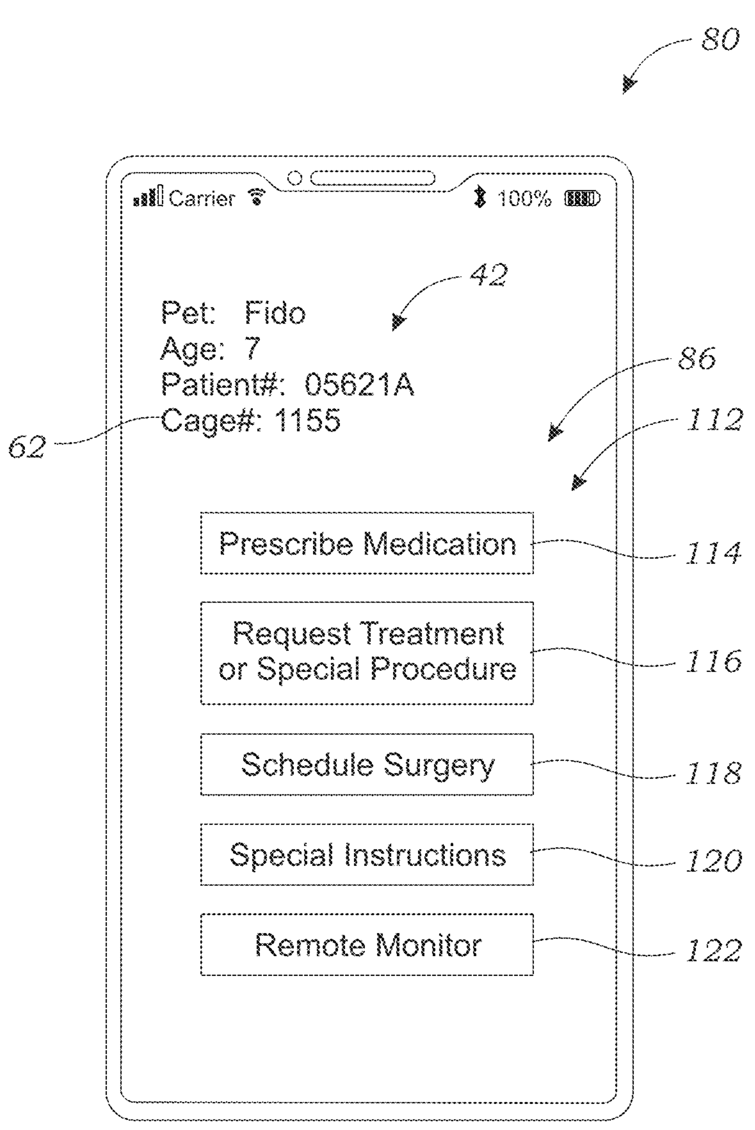
FIG. 9 is a front elevation view of a smart phone shown in FIG. 8 being used to update the system.

FIG. 9 is a front elevation view of the smart phone 80 shown in FIG. 8 being used to update the operation of the system 10 of FIG. 1. The term "smart phone" in this context is defined to include any form of computer device, typically but not necessarily portable, which may be used for entry of data and control of the system 10, including phones, tablets, laptops, etc.). As shown in FIG. 9, the smart phone 80 includes a display 108 for displaying animal information 36 (including cage number 62 where the animal is kept), as well as functional options 112 for controlling the system 10. In this case, this includes a prescribe medication function 114 for prescribing medication and course of treatment, a request function 116 for requesting a treatment or special procedure, a schedule surgery function 118, a special instructions function 120, and a remote monitor function 122 which may be used to remotely observe the animal, typically be streaming video from a camera (not shown) located near the cage 20.

This functionality may also be made accessible to the public, for purposes of pet adoption, etc. While this embodiment is shown to illustrate one embodiment of the software 86, those skilled in the art may devise a wide range of options which should be considered within the scope of the present invention.

Figure 10:
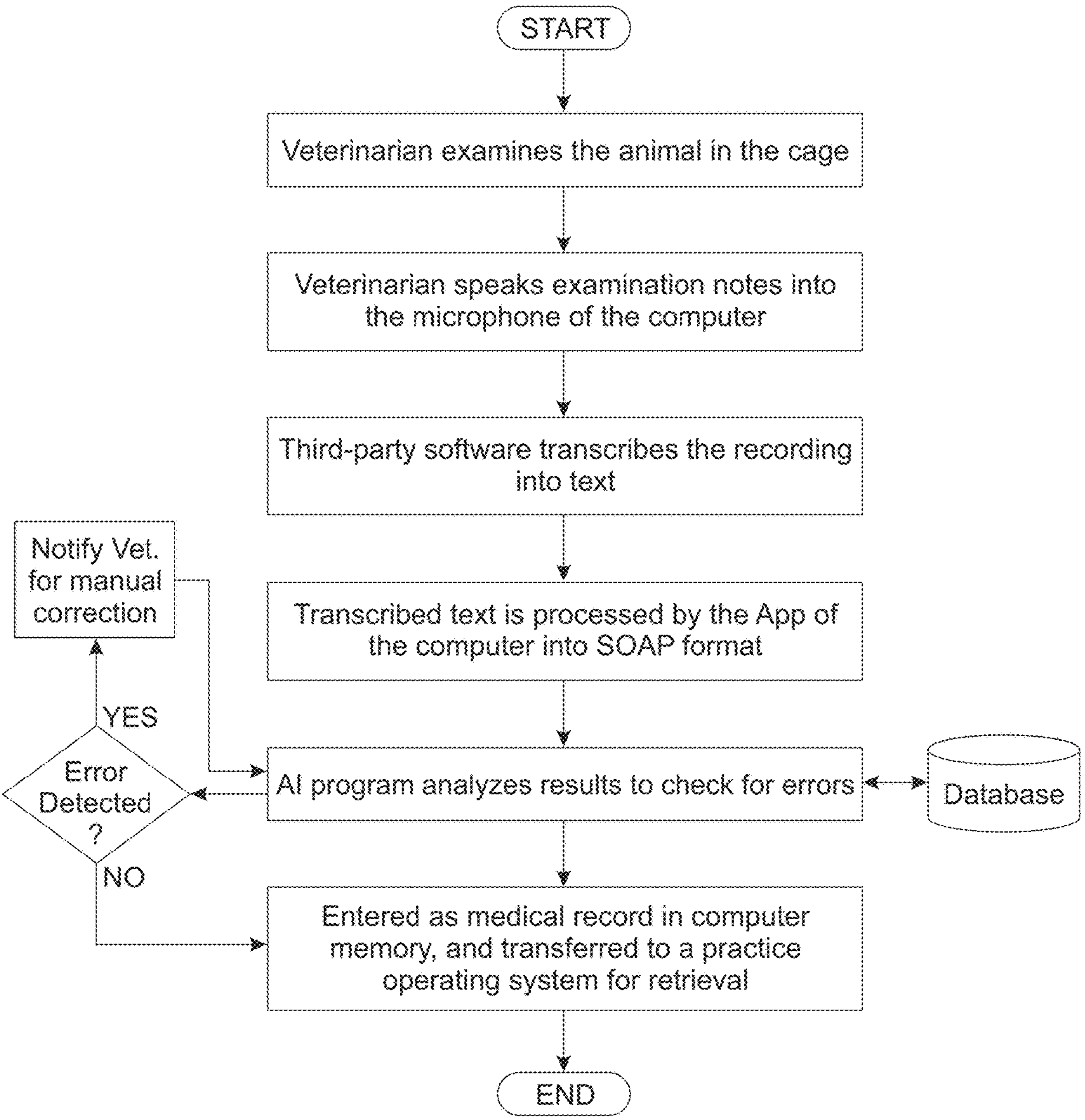
FIG. 10 is a flow diagram illustrating a voice-to-text feature of the system.

FIG. 10 is a flow diagram illustrating the voice-to-text feature of the system 10. As shown in FIG. 10, the system 10 is adapted to enable a veterinarian to conduct an exam on an animal within the cage 20, and utilize voice-to-text software and other components described below to enter a course of treatment into the system 10. In some embodiments, the caregiver may instead remove the computer 40 from the display panel 30, and remove the animal from the cage 20, and conduct an examination at a table or similar, instead of cage-side.

First, the veterinarian speaks examination notes into the microphone 96 of the computer 40 (shown in FIG. 8), wherein voice-to-text software (such as DRAGON®, etc.) transcribes the recording to text. The transcribed text is processed by the software 86 of the computer 40, where it undergoes further processing, discussed below.

In various embodiments, the caregiver does not need to type on the display screen 42 or on any additional devices, and can conduct a full examination of the animal with voice-only. For example, one of the computers 40 may be activated or "woken up" by a voice command, such as speaking the number of the associated cage (e.g., "activate cage 5"), the animal's name, or any other similar voice command that might be set by one skilled in the art, or by the user himself/herself. The voice command can also be used to retrieve identifying information or treatment information, e.g., "show me X-rays," or similar. The application/software 86 may be programmed to automatically return to a "home" screen (not shown) after a predetermined idle time, which may include a photo of the animal, basic information, or any other information desired by the user. The app 86 should automatically update information that has been edited/added by the veterinarian, remotely by the owner, or by another caregiver (e.g., adding invoice charges for services rendered, etc.). The computer 40 may also include a speaker (not shown) for providing audio responses to the caregiver. For example, the veterinarian may verbally ask a question and receive an audio response, or the audio response may sound after each command to confirm the input. Furthermore, the audio response may in some embodiments replace the warning LEDs 44, i.e., instead of a flashing light, the app 86 may sound an audio alert in the form of a tone, words, etc.

Next, the transcribed examination notes are processed by the software 86 of the computer 40, and further by the AI program 88 (which may include machine learning and other software). The software 86 may be in the form of an "app," but alternatively may be hosted on a web browser, or similar. The app processes the text into four components: Subjective, Objective, Assessment, and Plan (SOAP). SOAP is a structured format used in veterinary medicine to organize and document patient information during exams. The Subjective section covers subjective factors such how the patient appears (e.g., bright, alert, responsive, dull), while the Objective section includes all objective findings (e.g., vital signs, physical exam results). The Assessment summarizes the clinician's assessment of the patient's condition, and the Plan outlines the recommended treatment or next steps.

Importantly, the system 10 uses machine learning/AI to correctly organize all of this data into the correct format for the veterinarian, so that he or she does not have to organize the data themselves, while they are otherwise occupied with the animal. For example, the vet might mention the initial impression that the animal appears listless, a subjective note, and then also note that the animal has a heart rate (HR) of 65, an objective factor, and then more comments about subjective factors. Throughout the verbal notes, the vet may include notes about his/her assessment and plan, and the system 10 is able to sort this into SOAP format using machine learning techniques.

Next, the AI program 88 ensures consistency and accuracy, and may reference the database 106 of the central server 100 for progressive machine learning. The AI program 88 ensures the results of the exam are consistent with good medical practice. For example, it may note an error (or potential error) if a medication is input as the wrong dosage, such as if the animal is under the weight range for that amount, or similar, or if a suggested medication conflicts with another medication that the animal is already receiving. The AI program 88 may also flag allergies, past treatments, conflicting medications, health risks for the breed, etc., which the veterinarian may have missed. If there is an error, the veterinarian is notified for review. Once the veterinarian has reviewed, those results are then placed in the operating system of the cage 20 for use at the cage 20 at a later date by any of the staff. It also may be transferred to a practice operating system (such as EXYVET®) so it can retrieved, and it is stored as a medical record.

Embodiments of the animal treatment system 10 for veterinarian animal cages described in this specification differ from and improve upon currently existing options. In particular, some embodiments differ existing course of treatment practices for animals in veterinarian animal cages, which typically include hand-written notes or other informal information relay. While the course of treatment and medication information is normally stored digitally in a computing device by veterinarians, there is no existing system that ties together the digital information with the cages to be used as instruction for feeding and/or medicating. Furthermore, none of the existing veterinarian animal cages incorporated display panels 30 or warning lights 44 that can provide visual reminders to feed or medicate an animal in the cage 20.

In addition, some embodiments of the animal treatment system 10 for veterinarian animal cages improve upon the currently existing options by providing a display system that presents the relevant treatment and animal care information 36/38 in full view of anyone nearby the cage, and because the displayed information is driven by software, the information is coordinated with the course of treatment from the doctor. This is a vast improvement over existing veterinarian animal cage systems and treatment/care protocols which typically involve too much time to retrieve the information when it can be right there with the animal in question. The result is less confusion and less room for error in treatment.

The animal treatment system 10 for the animal cages of the present disclosure generally works by visually outputting a single course of treatment for the one animal occupying the cage, along with warning lights 44 that are triggered in time-synchronization with expressed timing of veterinarian directed feeding times or medication administration times, along with any other relevant information (e.g., change bandages daily). This assures that nothing will be missed by the veterinarian staff—feeding, medication, change of bandages, etc., are all digitally displayed and tied to the warning lights 44 (which can statically shine when triggered, or can be configured to flash when triggered) until the procedure is accomplished and reset.

In another embodiment, the App is also set up for text messaging (as well as emails and any other for s of communication) between the hospital/vet/staff and the pet owner. Each text message is displayed on the display screen of the cage, and may be further displayed on monitors elsewhere in the facility, so that staff are aware of the communications as soon as possible. Staff can text from the computer of any cage by awaking the cage: ex cage 5 send a text to the owner of animal X. The APP houses the text address and the text is made voice to text via the app and the digital cage display. All text messages may be retained by the app, associated with the animal's file, for future reference.

The title of the present application, and the claims presented, do not limit what may be claimed in the future, based upon and supported by the present application. Furthermore, any features shown in any of the drawings may be combined with any features from any other drawings to form an invention which may be claimed.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

What is claimed is:

1. A system for assisting a veterinarian in caring for an animal, the system comprising:

a veterinarian animal cage having a cage body and a door that allows access to the cage body;

a computer having a computer processor, a computer memory, a wireless data communication device, and a display screen, the computer being mounted on the veterinarian animal cage;

a central server having a computer processor and a computer memory, the central server being operably connected with the computer, the central server having a management program and a database installed in the computer memory for storing the information about the animals, and for transmitting information related to the animal housed in the veterinarian animal cage to the computer, so that the information may be visually outputted on the display screen;

wherein the computer receives input from the veterinarian, and transmits the input to the central server where it is stored in the database of the central server;

wherein the information transmitted to the computer includes a course of treatment for the animal housed in the veterinarian animal cage;

and wherein the computer is configured to provide a visual treatment warning at the veterinarian animal cage that is automatically triggered in time-synchronization with the course of treatment; and further comprising a cuboid housing upon which the digital display panel is pivotally mounted, the cuboid housing being physically mounted on the veterinarian animal cage, and the computer is slidably mounted on a retainer mechanism of the digital display panel.

2. The system of claim 1, wherein the computer receives the input from the veterinarian via the following step: receiving, via a microphone of the computer, verbal instruction from the veterinarian.

3. The system of claim 1, further comprising an AI program operably installed on the computer memory of the computer, wherein the AI program is adapted to check for errors in the input made by the veterinarian, and flag any errors for review.

4. The system of claim 1, further comprising a digital display panel mounted on the veterinarian animal cage, upon which the computer is mounted.

5. The system of claim 1, further comprising one or more colored warning LEDs mounted on the digital display panel, apart from the computer, which are operably connected to the computer to provide a visual warning alert that it is presently time to medicate, time to feed, not medicate/feed, when an animal is aggressive, or indicate a problem in vital signs of the animal.

6. The system of claim 1, wherein the computer device is operably connected to an adjustable-color light source positioned within the animal cage, and the computer device functions to adjust the color of the adjustable-color light source from white to another color to indicate a warning about the aggressiveness of the animal.

7. The system of claim 1, wherein the computer device is operably connected to an adjustable-color light source positioned within the animal cage, and the computer device functions to adjust the color of the adjustable-color light source from white to another color to indicate that the animal requires medication.

* * * * *